United States Patent [19]

Stanchi et al.

[11] Patent Number: 5,641,649
[45] Date of Patent: Jun. 24, 1997

[54] **EXPRESSION OF OSTEOGENIC FACTOR OP-1 IN CELLS OF *SPODOPTERA FRUGIPERDA* INFECTED WITH RECOMBINANT BACULOVIRUS**

[75] Inventors: Ombretta Stanchi, Travedona Monate; Alessandro Negro, Padua; Lanfranco Callegaro, Ponte di Brenta, all of Italy

[73] Assignee: Italian Ministry for Universities and Scientific and Technological Research, Rome, Italy

[21] Appl. No.: 256,368

[22] PCT Filed: Jan. 27, 1993

[86] PCT No.: PCT/EP93/00183

§ 371 Date: Sep. 22, 1994

§ 102(e) Date: Sep. 22, 1994

[87] PCT Pub. No.: WO93/15197

PCT Pub. Date: Aug. 5, 1993

[30] Foreign Application Priority Data

Jan. 27, 1992 [IT] Italy .................. PD92A0007

[51] Int. Cl.⁶ .................. C12P 19/34; C12P 21/06; C12N 5/00; C12N 15/00
[52] U.S. Cl. .................. 435/69.1; 435/91.2; 435/235.1; 435/348; 435/320.1; 935/32
[58] Field of Search .................. 435/69.1, 91.2, 435/235.1, 240.2, 320.1; 935/32

[56] References Cited

U.S. PATENT DOCUMENTS 5,155,037 10/1992 Summers .................. 435/240.2
5,221,620 6/1993 Purchio et al. .................. 435/69.7
5,244,793 9/1993 Purchio et al. .................. 435/69.4
5,322,774 6/1994 Peakman et al. .................. 435/69.1

FOREIGN PATENT DOCUMENTS 0127839 12/1984 European Pat. Off. .
9011366 10/1990 WIPO .
9105802 5/1991 WIPO .

OTHER PUBLICATIONS

Luckow et al, "Trends in the Development of Baculovirus Expression Vectors", *Bio/Technology 6*: 47–55 (Jan. 1988).
Celeste et al, "Identification of transfroming growth factor β family . . . " *PNAS 87*: 9843–9847 (Dec. 1990).
Madisen et al "Expression of the Human Immunodeficiency Virus gag Gene in Insect Cells", *Virology 158*: 248–250 (May 1987).

*Primary Examiner*—Stephen G. Walsh
*Assistant Examiner*—Daryl A. Basham
*Attorney, Agent, or Firm*—Birch, Stewart, Kolasch & Birch, LLP

[57] ABSTRACT

The present invention is directed towards a method of producing a DNA sequence encoding human osteogenic protein, OP-1, using recombinant DNA techniques. The DNA sequence encoding OP-1 is utilized in the preparation of recombinant baculovirus, which is then used to infect cells from *Spodoptera frugiperda*. The present invention is further drawn to the production of physiologically active OP-1 protein by culturing the infected insect cells and to recombinant baculovirus containing DNA encoding human OP-1 as well as insect cells infected with the recombinant baculovirus. The recombinant OP-1 produced by the present invention may be used to produce pharmaceutical compositions useful in the treatment of bone diseases, orthopedic diseases, bone defects, and trauma.

15 Claims, 4 Drawing Sheets

```
         10         20         30         40         50         60         70         80         90        100
ATGCACGTGC GCTCACTGCG AGCTGCGGCG GCGCCGCACA GCTTCGTGGC GCTCTGGGCA CCCCTGTTCC TGCTGCGCTC CGCCCTGGCC GACTTCAGCC
TACGTGCACG CGAGTGACGC TCGACGCCGC CGCGGCGTGT CGAAGCACCG CGAGACCCGT GGGGACAAGG ACGACGCGAG GCGGGACCGG CTGAAGTCGG 110        120        130        140        150        160        170        180        190        200
TGGACAACGA GGTGCACTCG AGCTTCATCC ACCGGCGCCT CCGCAGCCAG GAGCGGCGGG AGATGCAGCG CGAGATCCTC TCCATTTTGG GCTTGCCCCA
ACCTGTTGCT CCACGTGAGC TCGAAGTAGG TGGCCGCGGA GGCGTCGGTC CTCGCCGCCC TCTACGTCGC GCTCTAGGAG AGGTAAAACC CGAACGGGGT 210        220        230        240        250        260        270        280        290        300
CCGCCCGCGC CCGCACCTCC AGGGCAAGCA CAACTCGGCA CCCATGTTCA TGCTGGACCT GTACAACGCC ATGGCGGTGG AGGAGGGCGG CGGGCCCGGC
GGCGGGCGCG GCGTGGAGG TCCCGTTCGT GTTGAGCCGT GGGTACAAGT ACGACCTGGA CATGTTGCGG TACCGCCACC TCCTCCCGCC GCCCGGGCCG 310        320        330        340        350        360        370        380        390        400
GGCCAGGGCT TCTCCTACCC CTACAAGGCC GTCTTCAGTA CCCAGGGCCC CCCTCTGGCC AGCCTGCAAG ATAGCCATTT CCTCACCGAC GCCGACATGG
CCGGTCCCGA AGAGGATGGG GATGTTCCGG CAGAAGTCAT GGGTCCCGGG GGGAGACCGG TCGGACGTTC TATCGGTAAA GGAGTGGCTG CGGCTGTACC 410        420        430        440        450        460        470        480        490        500
TCATGAGCTT CGTCAACCTC GTGGAACATG ACAAGGAATT CTTCCACCCA CGCTACCACC ATCGAGAGTT CCGGTTTGAT CTTTCCAAGA TCCCAGAAGG
AGTACTCGAA GCAGTTGGAG CACCTTGTAC TGTTCCTTAA GAAGGTGGGT GCGATGGTGG TAGCTCTCAA GGCCAAACTA GAAAGGTTCT AGGGTCTTCC 510        520        530        540        550        560        570        580        590        600
GGAAGCTGTC ACGGCAGCCG AATTCCGGAT CTACAAGGAC TACATCCGGG AACGCTTCGA CAATGAGACG TTCCGGATCA GCGTTTATCA GGTGCTCCAG
CCTTCGACAG TGCCGTCGGC TTAAGGCCTA GATGTTCCTG ATGTAGGCCC TTGCGAAGCT GTTACTCTGC AAGGCCTAGT CGCAAATAGT CCACGAGGTC 610        620        630        640        650        660        670        680        690        700
GAGCACTTGG GCAGGGAATC GGATCTCTTC CTGCTCGACA GCCGTACCCT CTGGGCCTCG GAGGAGGGCT GGCTGGTGTT TGACATCACA GCCACCAGCA
CTCGTGAACC CGTCCCTTAG CCTAGAGAAG GACGAGCTGT CGGCATGGGA GACCCGGAGC CTCCTCCCGA CCGACCACAA ACTGTAGTGT CGGTGGTCGT 710        720        730        740        750        760        770        780        790        800
ACCACTGGGT GGTCAATCCG CGGCACAACC TGGGCCTGCA GCTCTCGGTG GAGACGCTGG ATGGGCAGAG CATCAACCCC AAGTTGGCGG GCCTGATTGG
TGGTGACCCA CCAGTTAGGC GCCGTGTTGG ACCCGGACGT CGAGAGCCAC CTCTGCGACC TACCCGTCTC GTAGTTGGGG TTCAACCGCC CGGACTAACC 810        820        830        840        850        860        870        880        890        900
GCGGCACGGG CCCCAGAACA AGCAGCCCTT CATGGTGGCT TTCTTCAAGG CCACGGAGGT CCACTTCCGC AGCATCCGGT CCACGGGGAG CAAACAGCGC
CGCCGTGCCC GGGGTCTTGT TCGTCGGGAA GTACCACCGA AAGAAGTTCC GGTGCCTCCA GGTGAAGGCG TCGTAGGCCA GGTGCCCCTC GTTTGTCGCG 910        920        930        940        950        960        970        980        990      1.000
AGCCAGAACC GCTCCAAGAC GCCCAAGAAC CAGGAAGCCC TGCGGATGGC CAACGTGGCA GAGAACAGCA GCAGCGACCA GAGGCAGGCC TGTAAGAAGC
TCGGTCTTGG CGAGGTTCTG CGGGTTCTTG GTCCTTCGGG ACGCCTACCG GTTGCACCGT CTCTTGTCGT CGTCGCTGGT CTCCGTCCGG ACATTCTTCG 1.010      1.020      1.030      1.040      1.050      1.060      1.070      1.080      1.090      1.100
ACGAGCTGTA TGTCAGCTTC CGAGACCTGG GCTGGCAGGA CTGGATCGCG CCTGAAGGCT ACGCCGCCTA CTACTGTGAG GGGGAGTGTG CCTTCCCTCT
TGCTCGACAT ACAGTCGAAG GCTCTGGACC CGACCGTCCT GACCTAGCGC GGACTTCCGA TGCGGCGGAT GATGACACTC CCCCTCACAC GGAAGGGAGA 1.110      1.120      1.130      1.140      1.150      1.160      1.170      1.180      1.190      1.200
GAACTCCTAC ATGAACGCCA CCAACCACGC CATCGTGCAG ACGCTGGTCC ACTTCATCAA CCCGGAAACG GTGCCCAAGC CCTGCTGTGC GCCCACGCAG
CTTGAGGATG TACTTGCGGT GGTTGGTGCG GTAGCACGTC TGCGACCAGG TGAAGTAGTT GGGCCTTTGC CACGGGTTCG GGACGACACG CGGGTGCGTC 1.210      1.220      1.230      1.240      1.250      1.260      1.270      1.280      1.290      1.300
CTCAATGCCA TCTCCGTCCT CTACTTCGAT GACAGCTCCA ACGTCATCCT GAAGAAATAC AGAAACATGG TGGTCCGGGC CTGTGGCTGC CACTAG
GAGTTACGGT AGAGGCAGGA GATGAAGCTA CTGTCGAGGT TGCAGTAGGA CTTCTTTATG TCTTTGTACC ACCAGGCCCG GACACCGACG GTGATC
```

Fig. 1

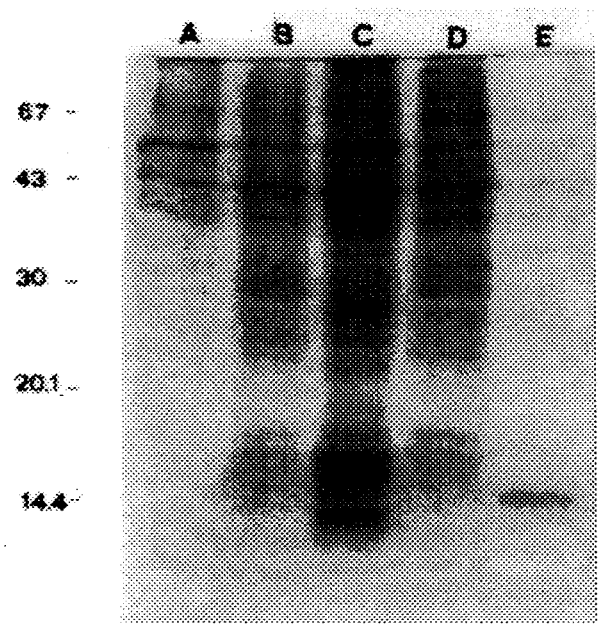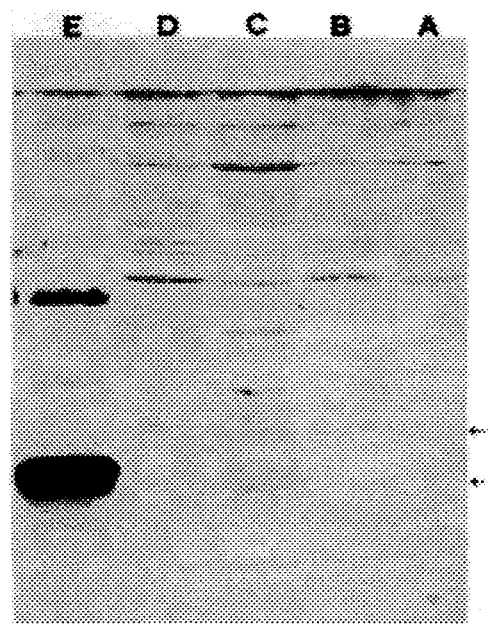

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1295 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:1:

```
ATGCACGTGC GCTCACTGCG AGCTGCGGCG GCGCCGCACA GCTTCGTGGC GCTCTGGGCA      60
CCCCTGTTCC TGCTGCGCTC CGCCCTGGCC GACTTCAGCC TGGACAACGA GGTGCACTCG     120
AGCTTCATCC ACCGGCGCCT CCGCAGCCAG GAGCGGCGGG AGATGCAGCG CGAGATCCTC     180
TCCATTTTGG GCTTGCCCCA CCGCCCGCGC CCGCACCTCC AGGGCAAGCA CAACTCGGCA     240
CCCATGTTCA TGCTGGACCT GTACAACGCC ATGGCGGTGG AGGAGGGCGG CGGGCCCGGC     300
GGCCAGGGCT TCTCCTACCC CTACAAGGCC GTCTTCAGTA CCCAGGGCCC CCCTCTGGCC     360
AGCCTGCAAG ATAGCCATTT CCTCACCGAC GCCGACATGG TCATGAGCTT CGTCAACCTC     420
GTGGAACATG ACAAGGAATT CTTCCACCCA CGCTACCACC ATCGAGAGTT CCGGTTTGAT     480
CTTTCCAAGA TCCCAGAAGG GGAAGCTGTC ACGGCAGCCG AATTCCGGAT CTACAAGGAC     540
TACATCCGGG AACGCTTCGA CAATGAGACG TTCCGGATCA GCGTTTATCA GGTGCTCCAG     600
GAGCACTTGG GCAGGGAATC GGATCTCTTC CTGCTCGACA GCCGTACCCT CTGGGCCTCG     660
GAGGAGGGCT GGCTGGTGTT TGACATCACA GCCACCAGCA ACCACTGGGT GGTCAATCCG     720
CGGCACAACC TGGGCCTGCA GCTCTCGGTG GAGACGCTGG ATGGGCAGAG CATCAACCCC     780
AAGTTGGCGG GCCTGATTGG GCGGCACGGG CCCCAGAACA AGCAGCCCTT CATGGTGGCT     840
TTCTTCAAGG CCACGGAGGT CCACTTCCGC AGCATCCGGT CCACGGGGAG CAAACAGCGC     900
AGCCAGAACC GCTCCAAGAC GCCCAAGAAC CAGGAAGCCC TGCGGATGGC CAACGTGGCA     960
GAGAACAGCA GCAGCGACCA GAGGCAGGCC TGTAAGAAGC ACGAGCTGTA TGTCAGCTTC    1020
CGAGACCTGG GCTGGCAGGA CTGGATCGCG CCTGAAGGCT ACGCCGCCTA CTACTGTGAG    1080
GGGGAGTGTG CCTTCCCTCT GAACTCCTAC ATGAACGCCA CCAACCACGC CATCGTGCAG    1140
```

```
ACGCTGGTCC  ACTTCATCAA  CCCGGAAACG  GGCCCAAGCC  CTGCTGTGCG  CCCACGCAGC      1200

TCAATGCCAT  CTCCGTCCTC  TACTTCGATG  ACAGCTCCAA  CGTCATCCTG  AAGAAATACA      1260

GAAACATGGT  GGTCCGGGCC  TGTGGCTGCC  ACTAG                                   1295
```

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO:2:

```
GAGGCGCAAA  AAATG                                                             15
```

( 2 ) INFORMATION FOR SEQ ID NO:3:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Escherichia coli ( x i ) SEQUENCE DESCRIPTION: SEQ ID NO:3:

```
TAACGAGGCG  CAAAAAATGA  AAAAGACAGC  TATCGCGATC  TTGGAGGATG  ATTAAATG        58
```

( 2 ) INFORMATION FOR SEQ ID NO:4:

( i ) SEQUENCE CHARACTERISTICS:
        ( A ) LENGTH: 68 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Autographa californica nuclear polyhedrosis
            virus ( i x ) FEATURE:
        ( A ) NAME/KEY: CDS
        ( B ) LOCATION: 56..68
        ( D ) OTHER INFORMATION: /note="Nucleotides 56-68 encompass,
            in condensed form, nucleotides 183-1083 of the 7.0 kb
            EcoR I fragment of the AcMNPV polyhedrin gene cloned
            into the EcoRI/Hind III sites of the pUC8 portion of
            pVL1392. See Figure 2."

( x i ) SEQUENCE DESCRIPTION: SEQ ID NO:4:

```
TATAAAATAT  TCCGGATTAT  TCATACCGTC  CCACCATCGG  GCGCGGATCC  TTTCTNNTAA      60
```

NNAATAAA                                                                                                68

( 2 ) INFORMATION FOR SEQ ID NO:5:

( i ) SEQUENCE CHARACTERISTICS:
          ( A ) LENGTH: 45 base pairs
          ( B ) TYPE: nucleic acid
          ( C ) STRANDEDNESS: double
          ( D ) TOPOLOGY: linear ( i i ) MOLECULE TYPE: other nucleic acid
          ( A ) DESCRIPTION: /desc ="5'- 3'strand of synthetic
          polylinker in pVL1392. See Figure 2."

( i i i ) HYPOTHETICAL: NO ( i v ) ANTI-SENSE: NO ( x i ) SEQUENCE DESCRIPTION: SEQ ID NO:5:

GATCAGATCT GCAGCGGCCG CTCCAGAATT CTAGAAGGTA CCCGG                                                        45

( 2 ) INFORMATION FOR SEQ ID NO:6:

( i ) SEQUENCE CHARACTERISTICS:
          ( A ) LENGTH: 45 base pairs
          ( B ) TYPE: nucleic acid
          ( C ) STRANDEDNESS: double
          ( D ) TOPOLOGY: linear ( i i ) MOLECULE TYPE: other nucleic acid
          ( A ) DESCRIPTION: /desc ="complementary 3'-5'strand of
          synthetic polylinker in pVL1392. See Figure 2."

( i i i ) HYPOTHETICAL: NO ( i v ) ANTI-SENSE: NO ( x i ) SEQUENCE DESCRIPTION: SEQ ID NO:6:

GATCCCGGGT ACCTTCTAGA ATTCTGGAGC GGCCGCTGCA GATCT                                                        45

( 2 ) INFORMATION FOR SEQ ID NO:7:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="PCR primer"

( i i i ) HYPOTHETICAL: NO ( i v ) ANTI-SENSE: NO ( x i ) SEQUENCE DESCRIPTION: SEQ ID NO:7:

TTGATGCTCT GCCCATCCAG CGT                                                                               23

( 2 ) INFORMATION FOR SEQ ID NO:8:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="PCR primer"

( i i i ) HYPOTHETICAL: NO ( i v ) ANTI-SENSE: NO ( x i ) SEQUENCE DESCRIPTION: SEQ ID NO:8:

CATGCTGGAC CTGTACAACG CCAT                                                                                          24

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR primer"

( i i i ) HYPOTHETICAL: NO ( i v ) ANTI-SENSE: NO ( x i ) SEQUENCE DESCRIPTION: SEQ ID NO:9:

GTGGTCAATC CGCGGCACAA CCTG                                                                                          24

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR primer"

( i i i ) HYPOTHETICAL: NO ( i v ) ANTI-SENSE: NO ( x i ) SEQUENCE DESCRIPTION: SEQ ID NO:10:

AGGATCCAGC TAGTGGCAGC CACAGG                                                                                        26

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR primer"

( i i i ) HYPOTHETICAL: NO ( i v ) ANTI-SENSE: NO ( x i ) SEQUENCE DESCRIPTION: SEQ ID NO:11:

AATCTAGAAT GCACGTGCGC TCCAC                                                                                         25

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR primer"

( i i i ) HYPOTHETICAL: NO ( i v ) ANTI-SENSE: NO (x i) SEQUENCE DESCRIPTION: SEQ ID NO:12:

GGTGGCGACG ACTCCTGGAG CCCG                                                          24

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="PCR primer"

(i i i) HYPOTHETICAL: NO (i v) ANTI-SENSE: NO (x i) SEQUENCE DESCRIPTION: SEQ ID NO:13:

CACTCGAGCT TCATCCACCG GCGCC                                                         25

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="PCR primer"

(i i i) HYPOTHETICAL: NO (i v) ANTI-SENSE: NO (x i) SEQUENCE DESCRIPTION: SEQ ID NO:14:

AGCTCGAGTG CACCTCGTTG TCCAGGCTGA A                                                  31

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="PCR primer"

(i i i) HYPOTHETICAL: NO (i v) ANTI-SENSE: NO (x i) SEQUENCE DESCRIPTION: SEQ ID NO:15:

TTGTAGGGGT AGGAGAAGCC CTG                                                           23

EXPRESSION OF OSTEOGENIC FACTOR OP-1 IN CELLS OF *SPODOPTERA FRUGIPERDA* INFECTED WITH RECOMBINANT BACULOVIRUS

BACKGROUND OF THE INVENTION

1. Field of the Invention

The present invention relates to a process for obtaining human osteogenic protein, OP-1, via recombinant DNA technology. This process is exemplified by infecting cells of *Spodoptera frugiperda* with a recombinant baculovirus to produce the mature, biologically active form of OP-1.

2. Description of Related Art

A. OSTEOGENIC FACTOR OP-1

Osteogenic factor OP-1 belongs, in view of its biological activity, to the family of Bone Morphogenic Proteins (BMPs), which are factors responsible for the induction of cartilage and bone.

BMPs form part of the large superfamily of TGF-β (Transforming Growth Factor β), a family that includes embryonic morphogens, endocrine function regulators, wide-range regulators, and regulators that are specific for cell proliferation and differentiation.

TGF-β is a prototype of this family. It is a dimer of two identical chains of 112 amino acids held together by disulfide bridges. Each chain is synthesized starting from a longer precursor of about 390 amino acids which has the characteristics of a secretory polypeptide, presenting a hydrophobic sequence in the N-terminal region which should function as a secretory peptide for the secretion of the molecule. The precursor is then processed to its mature form by cleavage by a specific peptidase, which cleaves four basic amino acids immediately prior to the biologically active domain. The precursor region plays an essential role in the correct folding of the mature portion in vivo, to the extent that to date, no mature, biologically active peptides are known to have been produced in *Escherichia coli* by recombinant DNA techniques.

These factors are known in various animal species from Drosophila to humans, their sequences having been maintained to a great extent throughout evolution. The sequence homology among the various polypeptides is very high, and resides mainly in the C-terminal region. The degree of identity of sequence varies between 25 and 90% among the various family members. In this region, between 7 and 9 cysteines are conserved among all the members. These are involved in the formation of disulfide bridges between the amino-acid chains.

BMPs induce chemotactic, proliferative and differential responses, which culminate in the transient formation of cartilage, followed by the accumulation of bone with hematopoietic marrow. The activity of BMPs has been characterized as strictly linked with the demineralized bone matrix, and is extractable with denaturing agents. They have in fact been extracted from various species including humans, monkeys, cattle, rats and mice (Sampath, T. K., Reddi, A. H. 1983, *PNAS* 80, 6591–6595; Urist, M. D. et al. 1979, *PNAS* 76, 1828–1832). Most studies were carried out on BMPs derived from bovine bone, an abundant and easily obtainable source.

In 1988 Wozney et al. (Wozney, J. M. et al., 1988, *Science* 242, 1528–1534) recovered a biologically active protein fraction of about 30 kD from bovine bone that could be detected by polyacrylamide gel electrophoresis under non-reducing conditions. Following reduction of the disulfide bridges by chemical methods, polypeptides of 30, 18 and 16 kD were obtained (Wang, E. A. et al., 1988, *PNAS* 85, 9484–9488). This protein fraction was digested with trypsin, and the peptides obtained were separated by HPLC and sequenced. This information was used in the synthesis of DNA probes which were used to identify the bovine genome sequences encoding the various factors. Using portions of these sequences as probes, the human sequences coding for the homologous factors were obtained.

Much is now known about these factors (Wozney, J. M. et al., 1990, *J. Cell. Sci.* Suppl. 13, 149–156; Wozney, J. M., 1989, *Progress in Growth Factor Research*, 1, 267–280). Some were obtained via recombinant DNA techniques. Some examples of patents on growth factors belonging to the abovesaid classes, obtained by recombinant DNA techniques, include EP 409472, WO 9011366, WO 8800205, EP 212474, WO 9105863, and U.S. Pat. No. 4,743,679.

OP-1, like all the members of the superfamily TGF-β, consists of a precursor sequence almost four times larger than the mature protein, which resides only in the C terminal portion. The nucleotide sequence of the human cDNA of 1294 base pairs has been published (Ozkaynak, E. et al. 1990, *EMBO J.* 9, 2085–2093).

The amino acid sequence of OP-1 consists of 431 amino acids, while the mature portion contains approximately 300 amino acids. There are four potential N-glycosylation sites, three of which are present in the mature region. In this region, seven cysteines are present, which characterize the entire superfamily, and allow the formation of disulfide bridges between the monomers. The molecular weight of the dimer is about 30 kD. Following chemical reduction and electrophoresis, this gives rise to two glycosylated bands of 16–18 kD (Sampath, T. K. et al., 1990, *JBC* 265, 13198–13205). The mature protein proved to have osteoinductive activity in vivo, using the model of induction in an ectopic site in rat. This test, which mimics the reparative cascade of a fracture, makes it possible to monitor histologically the formation of cartilage and bone and to measure the activity of the alkaline phosphatase during this process (Sampath T. K. et al., 1990, cited above).

B. RECOMBINANT DNA TECHNOLOGY

Recombinant DNA technology allows the construction of vectors that are capable of expressing proteins of interest in large quantities.

Recombinant DNA technology allows the molecular biologist to assemble DNA sequences with the aim of creating hybrid molecules capable of producing the molecules of interest. The method involves various reactions such as cutting with restriction enzymes, joining the fragments thus obtained by ligases, chemical synthesis of the oligonucleotides to be assembled, and various other methods (Sambrook, J. et al., *Molecular Cloning. A Laboratory Manual*, Second Edition, Cold Spring Harbor Laboratory Press, N.Y., 1989).

In order to obtain high levels of expression, the DNA elements to be assembled must contain certain essential items of information. These include, for example, a replication origin, resistance to an antibiotic, an expression promoter, transcription activators for the gene of interest, and other elements known to those of ordinary skill in the art. The appropriate combination of these elements produces a vector, and, if the gene of interest is functionally inserted with respect to the regulatory transcription and translation sequences, the resulting vector is called an expression vector. This plasmid or expression vector is capable of expressing the protein of interest in host cells. The protein can then be extracted by various processes.

The elements (promoters) which naturally control the expression of many genes, such as growth factors, are not very strong, and are only activated under suitable natural conditions which are often unknown. In order to overcome this obstacle, promoters with known activity are used, such as that of the polyhedrin gene of baculovirus, or other promotor sequences. The elements which are used for high levels of expression are therefore a combination of DNAs of various origin (eukaryotic, bacterial, viral, etc.) finally linked together to form a hybrid molecule. The transcription and translation of a gene depends on there being a suitable distance between the regulatory and coding sequences.

Based on this premise, one of the best ways for regulatory sequences to work is that the introduced gene be placed in the same position as the natural gene. One system used is that in which the regulatory sequences also include some amino acids of the coding sequences. Union with the introduced gene gives rise to a fused protein. If the fused portion is then removed, it is possible to obtain higher biological activity. If the fusion protein technique is not used, conventional techniques to obtain genes situated in close proximity to regulatory sequences depend on there being suitable restriction sites which allow them to be cloned. If there are no compatible sites in the vicinity, it is possible to obtain union of the segments by synthesis of an oligonucleotide or linker which contains the desired restriction site. If there are no restriction sites in the vicinity to allow the use of linkers, then it is possible to use the technique of deletion of DNA with the enzymes Bal31 or S1. This possibility does not allow for precise deletion, and each time various clones must be sequenced to see which is the most suitable. These systems are very limiting to the molecular biologist, and consequently, alternative strategies were developed, based on new techniques such as the Polymerase Chain Reaction (PCR) (Saiki et al., 1988 *Science* 239, 487; Scharf, S. J., 1986 *Science* 233, 1076).

By this technique, it is possible to amplify a gene segment up to a million times. The principle is based on the use of two oligonucleotides which can be paired by placing one on each of the strands of DNA to be amplified. The distance between the two oligonucleotides and the gene sequence in question will determine the length of the molecule produced. These two oligonucleotides are so constructed that there is a restriction site within their sequence which will allow for subsequent cloning. This restriction site is either naturally present, or is constructed ad hoc degenerating the minimum number of bases. This approach, called site-directed mutagenesis, allows the construction of restriction sites in the position which the molecular biologist has previously decided on. The construction of sites compatible with other gene segments allows for easy cloning on the one hand, but more importantly, on the other, it makes it possible to join various gene fragments in a more precise manner. This technique can be defined as direct mutagenesis cloning. In practice, by recombinant DNA technology, it is possible to express complete heterologous polypeptides by direct expression, or alternatively, to express the heterologous polypeptide fused to a portion of the amino acid sequence of an analogous polypeptide. In general, products obtained in the latter way are not biologically active (British Patent Application Publ. No. 2007676A; Wenzel, 1980 *American Scientist* 68, 664).

SUMMARY OF THE INVENTION

The possibility of isolating the human gene coding for an osteoinductive factor facilitates the understanding of bone diseases and orthopedic problems such as osteoporosis, osteoarthritis and slow-healing fractures, for which the search for a solution or preventive measures has proved to be an arduous task. OP-1 can be used in all those conditions in which it is important to induce and/or favor the formation, repair and regeneration of bones and/or cartilage.

By employing recombinant DNA technology it is possible to obtain a sufficient quantity of protein to help clarify the mechanisms of action of any one factor or combination of factors, for example to increase bone mass. Such factors could be associated with a biomaterial as a controlled release system, or as a filler.

Of the various systems for the expression of heterologous proteins, the most widely used, especially since it is the most economical, is expression in prokaryotic cells of *Escherichia coli*. This system is not always practicable as, although it faithfully reproduces the linear sequence of the amino acids comprising the protein, it does not allow for correct folding. This system can be useful to produce small proteins or peptides (as diagnostic antigens or vaccine components), the use of which does not require a specific conformation. Moreover, expression in *E. coli* is not able to confer on recombinant proteins many post-translational modifications characteristic of eukaryotic proteins, such as glycosylation and the formation of inter- and intra-molecular disulfide bridges. For OP-1, it is important that these modification systems be active, so as to obtain a biologically active osteoinductive factor.

In eukaryotic cells, expression in insect cell lines, by infection with recombinant baculovirus, facilitates high levels of expression (Luckow, V. A. and Summers, M. D., 1988 *Biotechnology* 6, 47–55), while maintaining biological activity thanks to the aforesaid post-translational modifications. From an industrial point of view, this system offers the advantage of employing a cell line which grows very well in serum-free medium, thus saving time and money in the purification of recombinant proteins.

Using recombinant DNA technology, the present inventors constructed a vector for use with baculovirus to infect cells of *Spodoptera frugiperda*. This vector contains cDNA encoding osteoinductive factor OP-1.

The PCR technique was employed for cloning, and by this method, restriction sites were created such that the distance between the regulatory sequences and the coding sequence was as natural as possible, facilitating easy cloning in the transfer vector pVL1392. DNA encoding human osteoinductive protein OP-1 was placed under the control of the promoter for the polyhedrin gene of baculovirus.

This construct was then cotransfected into *Spodoptera frugiperda* cells together with the natural baculovirus AcM-NPV (*Autographa californica* multiple nuclear polyhedrosis virus). The recombinant virus thus obtained, which carries the OP-1 gene under the control of the polyhedrin promoter and all the sequences involved in its synthesis, was purified and amplified. It was then employed to infect cells of *Spodoptera frugiperda* in order to express this heterologous protein.

Accordingly, it is an object of the present invention to provide a method for producing a DNA sequence encoding osteogenic protein, Op-1, comprising:

(a) amplifying, by the polymerase chain reaction technique, successive or successive overlapping fragments of DNA encoding OP-1 by employing appropriately spaced oligonucleotide primers encoding restriction endonuclease sites; and (b) assembling said fragments by recombinant DNA techniques to produce a DNA sequence encoding osteogenic protein, OP-1.

Another object of the present invention is to provide a method for preparing a recombinant baculovirus, comprising:

(a) inserting a DNA sequence encoding OP-1 into a baculovirus transfer vector to produce a transfer vector containing said DNA sequence;

(b) cotransfecting an insect cell with said transfer vector containing said DNA sequence of step (a) and wild-type *Autographa californica* multiple nuclear polyhedrosis virus, AcMNPV, viral DNA; and (c) recovering recombinant baculovirus containing said DNA sequence encoding OP-1.

Another object of the present invention is to provide a recombinant baculovirus, comprising a DNA sequence encoding human osteogenic protein, OP-1, functionally linked to regulatory elements necessary for the expression of OP-1 in insect cells infected with said recombinant baculovirus.

Yet another object of the present invention is to provide transfer vector pVL-OP1.

A further object of the present invention is to provide an insect cell harboring a recombinant baculovirus prepared by:

(a) inserting a DNA sequence encoding OP-1 into a baculovirus transfer vector to produce a transfer vector containing said DNA sequence;

(b) cotransfecting an insect cell with said transfer vector containing said DNA sequence of step (a) and wild-type *Autographa californica* multiple nuclear polyhedrosis virus, AcMNPV, vital DNA; and (c) recovering recombinant baculovirus containing said DNA sequence encoding OP-1.

A further object of the present invention is to provide a method for producing osteogenic protein, OP-1, by a method comprising:

(a) inserting a DNA sequence encoding OP-1 into a vector;

(b) inserting said vector of step (a) into a host cell;

(c) culturing said host cell of step (b); and (d) recovering maid OP-1 produced during said culturing of step (c).

Yet a further object of the present invention is to provide a method for producing osteogenic protein, OP-1, by a method comprising:

(a) inserting a DNA sequence encoding said OP-1 into a transfer vector capable of introducing said sequence into the genome of baculovirus, thereby producing recombinant baculovirus;

(b) introducing said recombinant baculovirus into an insect cell;

(c) culturing said insect cell harboring said recombinant baculovirus; and (d) recovering said OP-1 expressed during said culturing of step (c).

A still further object of the present invention is to provide a pharmaceutical composition, wherein said pharmaceutical composition comprises osteogenic protein, OP-1, and a pharmaceutically acceptable carrier. Said OP-1 can be produced by either of the methods described supra.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which:

FIG. 1 shows the nucleotide sequence of osteoinductive factor OP-1 (SEQ. I.D. NO.: 1)

FIG. 4a shows the electrophoretic pattern under reducing conditions of proteins obtained from cells of *Spodoptera frugiperda* infected with recombinant baculovirus containing DNA encoding human OP-1 protein.

FIG. 4b shows the results of Western Blotting using antipeptide antibody 300-320.

Figure 2:
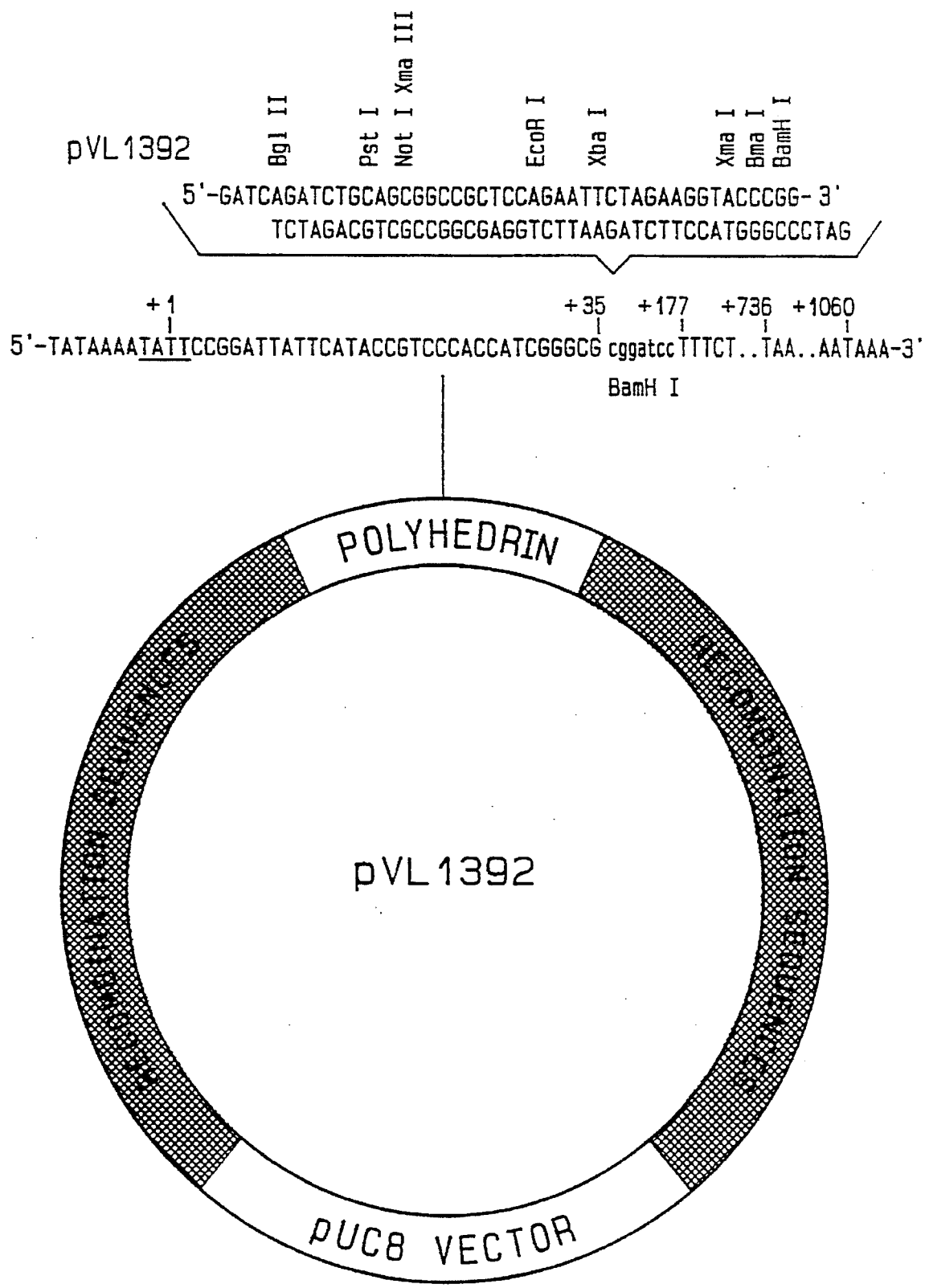
FIG. 2 is a map of vector pVL1392.

A: Supernatant of a culture of Sf9 cells infected with recombinant baculovirus (natural virus and vector pVL-OP1).

B: Cell pellet of a culture of Sf9 cells infected with recombinant baculovirus (natural virus and vector pVL-OP1).

C: cell pellet of sample B, frozen, thawed, and centrifuged.

D: Supernatant of sample C.

E: Mature portion of OP-1 induced in *Escherichia coli*.

DETAILED DESCRIPTION OF THE INVENTION

The following detailed description is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited in the present application are herein incorporated by reference in their entirety.

Recombinant DNA Techniques

Restriction enzymes were employed to cleave DNA according to the manufacturer's specifications. In general, 1 μg of plasmid was cut with 1 U of enzyme in 20 μl of solution. The temperature and the incubation time depended on the enzyme Used, but were generally 1 hour at 37° C. After incubation, the plasmids and gene fragments were purified in LMP agarose (BRL, U.S.A.) or Nu-Sieve agarose (FMC Marine Colloids, U.S.A.) in 40 mM Tris-HCl, 20 mM sodium acetate, 1 mM EDTA, and then eluted from the agarose with a Geneclean™ Kit (BIO101 Inc., La Jolla, Calif., U.S.A.).

To refill the 5' ends, the DNA was treated for 15 minutes at 15° C. with 10 U of Klenow polymerase. The DNA cut with the restriction enzymes was dephosphorylated with calf intestine alkaline phosphatase (Promega). The reaction was conducted using 1 U of alkaline phosphatase in 20 μl at 37° C. for 30 minutes. The ligation reaction was effected with T4 ligase at a concentration of 1 U per 0.5 μg of DNA in a reaction volume of 20 μl at 13° C. for 16 hours.

The constructs obtained were transformed into *E. coli* HB101, and transformed cells were selected on LB (Luria Bertani) Agar medium containing 100 μg/ml ampicillin. The plasmid DNA of the transformed cells obtained was purified by alkaline lysis for small preparations and with a Quiagen kit (DIAGEN GmbH, Düsseldorf, Germany). The expression vectors were prepared from the bacterial cells by the Quiagen method.

DNA probes were labelled with radioactive phosphorus $^{32}P$ with a Multiprime DNA labelling system from Amersham. The labelled isotope was acquired from the same manufacturer. The sequence of the constructs was checked for correctness by sequencing the DNA with a Sequenase® 2.0 kit (USB Corporation).

DNA AND PROTEINS FOR HUMAN OSTEOGENIC FACTOR OP-1

Each of the nucleic acid sequences and polypeptide disclosed herein, or their biologically functional equivalents, can be used in accordance with the present invention. The term "biologically functional equivalents," as used herein, denotes nucleic acid sequences or polypeptides exhibiting the same or similar biological activity as the particular nucleic acid sequences and polypeptide described infra.

For example, the nucleic acid sequences depicted herein can be altered by substitutions, additions or deletions that provide for biologically functionally equivalent molecules. Due to the degeneracy of the genetic code, other DNA sequences which encode substantially the same amino acid sequences may be used in the practice of the present invention. These include, but are not limited to, nucleotide sequences comprising all or portions of the OP-1 cDNA depicted below which are altered by the substitution of different codons that encode a physiologically functionally equivalent amino acid residue within the sequence, thus producing a silent change. Similarly, the OP-1 protein, or derivatives thereof, of the present invention include, but are not limited to, those containing all of the naturally-occurring amino acids, including altered sequences in which functionally equivalent amino acid residues are substituted for residues within the sequence, resulting in a silent change. For example, one or more amino acid residues within the sequence can be substituted with another amino acid of similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The recombinant OP-1 encoding nucleic acid sequences of the present invention may be engineered so as to modify processing or expression of OP-1. For example, and not by way of limitation, a signal sequence may be inserted upstream of OP-1 encoding sequences to permit secretion of OP-1, thereby facilitating harvesting or bioavailability.

Additionally, OP-1 can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including, but not limited to, in vitro site-directed mutagenesis (Hutchinson et al. (1978) *J. Biol. Chem.* 253:6551), use of TAB® linkers (Pharmacia), etc.

EXPRESSION VECTORS FOR HUMAN OP-1

Vectors contemplated for use in the present invention include those into which a DNA sequence as discussed below can be inserted, along with any necessary operational elements. Such vectors can then be subsequently transferred into a host cell and replicated therein. Preferred vectors are those whose restriction sites have been well documented and which contain the operational elements preferred or required for transcription of the DNA sequence.

Certain embodiments of the present invention employ vectors which would contain one or more of the DNA sequences described herein. It is preferred that all of these vectors have some or all of the following characteristics: (1) possesses a minimal number of host-organism sequences; (2) be stably maintained and propagated in the desired host; (3) be capable of being present in high copy number in the desired host; (4) possess a regulatable promoter positioned so as to promote transcription of the DNA of interest; (5) have at least one marker DNA sequence coding for a selectable trait present on a portion of the plasmid separate from that where the DNA sequence will be inserted; and (6) contain a DNA sequence capable of terminating transcription.

Cloning vectors capable of expressing the DNA sequences of the present invention contain various operational elements. These "operational elements" can include at least one promoter, at least one Shine-Dalgarno sequence and initiator codon, and at least one termination codon. These "operational elements" may also include one or more of the following: at least one operator, at least one leader sequence for proteins to be exported from intracellular space, at least one gene for a regulator protein, and any other DNA sequences necessary or preferred for appropriate transcription and subsequent translation of the cloned OP-1 DNA.

Certain of these operational elements may be present in the preferred vectors of the present invention. It is contemplated that any additional operational elements which may be required may be identified and added to these vectors using methods known to those of ordinary skill in the art, such as those described by Sambrook et al., supra.

Regulators

Regulators serve to prevent expression of the DNA sequence in the presence of certain environmental conditions and, in the presence of other environmental conditions, will allow transcription and subsequent expression of the protein coded for by the OP-1 DNA sequences. Regulatory segments may be inserted into the vector such that expression of the DNA sequence will not occur, or will occur to a greatly reduced extent, in the absence of inducer.

Promoters

Expression vectors can contain promoters which can be used by the host organism for expression of its own proteins.

Transcription Terminators

Transcription terminators serve to stabilize the vector. Such sequences have been described by Rosenberg et al. (1979) *Ann. Rev. Genet.* 13:319–353.

Non-translated Sequences

It is sometimes desirable to construct the 3' or 5' end of the coding region to allow incorporation of 3' or 5' non-translated sequences into the gene transcript. Included among these non-translated sequences are those which stabilize mRNA, as disclosed by Schmeissner et al. (1984) *J. Mol. Biol.* 176:39-53.

Ribosome Binding Sites

The microbial expression of foreign proteins requires operational elements which include ribosome binding sites. A ribosome binding site is a sequence which a ribosome recognizes and binds to in the initiation of protein synthesis as set forth in Gold et al. *Ann. Rev. Microbiol.* 35:557-580 and Marquis et al. (1986) *Gene* 42:175-183. A preferred ribosome binding site is GAGGCGCAAAAA(ATG) (SEQ. I.D. NO.: 2)

Leader Sequences and Translational Couplers

Additionally, it is sometimes preferred that DNA coding for an appropriate secretory leader (signal) sequence be present at the 5' end of the DNA sequence, as set forth by Watson, M. E. in *Nucleic Acids Res.* 12:5145-5163, if the protein is to be excreted from the host cytoplasm. The DNA for the leader sequence must be in a position that allows the production of a fusion protein in which the leader sequence is immediately adjacent to and covalently joined to OP-1, i.e., there must be no transcription or translation signals between the two DNA coding sequences.

In some species of host microorganisms, the presence of an appropriate leader sequence will allow transport of the completed protein into the periplasmic space, as in the case of some *E. coli*. In the case of certain *E. coli*, Saccharomyces, and strains of Bacillus and Pseudomonas, the appropriate leader sequence allows transport of the protein through the cell membrane and into the extracellular medium. In this situation, the protein may be purified from extracellular protein.

An additional DNA sequence can be located immediately preceding the DNA sequence which codes for the protein of interest. The additional DNA sequence is capable of functioning as a translational coupler, i.e., it is a DNA sequence that encodes an RNA which serves to position ribosomes immediately adjacent to the ribosome binding site of the inhibitor RNA with which it is contiguous. The translational coupler may be derived using the DNA sequence TAAC-GAGGCGCAAAAAATGAAAAAGACAGC-TATCGCGATCTTGGAGGATGATTA AATG (SEQ. I.D. NO.: 3) and methods currently known to those of ordinary skill in the art related to translational couplers.

Translation Terminators

Translation terminators serve to stop the translation of mRNA. They may be either natural, as described by Kohli, J., *Mol. Gen. Genet.* 182:430-439, or synthetic, as described by Pettersson, R. F. (1983) *Gene* 24:15-27.

Selectable Markers

Additionally, it is preferred that cloning vectors contain a selectable marker, such as a drug resistance marker or other marker which causes expression of a selectable trait by the host organism. The gene for ampicillin resistance can be included in the vector. In other plasmids, the gene for tetracycline resistance or the gene for chloramphenicol resistance can be included.

Such a drug resistance or other selectable marker facilitates the selection of transformants. Additionally, the presence of such a selectable marker in a cloning vector may be of use in keeping contaminating organisms from multiplying in the culture medium.

The operational elements discussed herein are routinely selected by those of ordinary skill in the art in light of prior literature and the teachings contained herein. General examples of these operational elements are set forth in B. Lewin (1983) *Genes*, Wiley & Sons, New York. Various examples of suitable operational elements may be found in the vectors discussed above, and may be gleaned via review of the publications discussing the basic characteristics of the aforementioned vectors.

Upon synthesis and isolation of all the necessary and desired component parts, the vector can be assembled by methods generally known to those of ordinary skill in the art. Assembly of such vectors is within the ordinary skill in the art, and, as such, is capable of being performed without undue experimentation.

Multiple copies of the DNA sequences of the present invention and their accompanying operational elements may be inserted into each vector. In such case, the host organism would produce greater amounts per vector of the desired protein. The number of multiple copies of the DNA sequence Which may be inserted into the vector is limited only by the ability of the resultant vector, due to its size, to be transferred into and replicated and transcribed in an appropriate host cell.

Host Cells

Vectors suitable for use in a variety of microorganisms and mammalian and insect cells are also routinely used in the art. Such microorganism include, for example, Bacillus, Pseudomonas, and yeast. The expression of proteins of interest in mammalian cells, including, for example, Chinese Hamster Ovary cells, is also well known in the art.

For expression in Bacillus, preferred vectors should include a regulated promoter such as the alpha amylase promoter, the subtilisin promoter, the P-43 promoter, or the spac-126 promoter. Useful transcription terminators include rrn and rrn BT.T. Transcriptional start sites and leader peptides can be chosen from among those from *B. amyloliquefaciens* neutral protease, *B. amyloliquefaciens* alpha-amylase, and *B. subtilis* subtilisin. Useful antibiotic markers are Kan$^r$ and Cam$^r$. Ribosome binding sites can be obtained from the *B. amyloliquefaciens* neutral protease and *B. amyloliquefaciens* alpha-amylase genes. A preferred expression system in hosts of the genus Bacillus involves the use of plasmid pUB110 as the cloning vehicle.

For expression in Pseudomonas, promoters can be selected from Trp, Lac, and Tac. Useful transcriptional start sites and leader peptides can be obtained from the phospholipase C and exotoxin A genes. Useful antibiotic markers are those for sulfonamides and streptomycins. A useful ribosome binding site can be obtained from the Trp promoter of *E. coli*. Particularly preferred vectors would employ the plasmid RSF1010, and derivatives thereof.

In the case of yeast, useful promoters include Gal 1 and 10, Adh 1 and 11, and Pho 5. Transcription terminators can be chosen from among Cyc, Una, Alpha Factor, and Sac 2. Transcriptional start sites and leader peptides can be obtained from the invertase, acid phosphatase, and Alpha factor genes. Useful selection markers are Ura 3, Leu 2, His 3, and Tap 1.

Finally, in the case of expression in mammalian cells, the DNA encoding the protein of interest should have a sequence efficient at binding ribosomes. Such a sequence is described by Kozak in *Nucleic Acids Research* (1987) 15:8125–8132. The protein-encoding fragment can be inserted into an expression vector containing a transcriptional promoter and a transcriptional enhancer as described by Guarente in *Cell* (1988) 52:303–305 and Kadonaga et al. (1987) *Cell* 51:1079–1090. A regulatable promoter as in the Pharmacia plasmid pMSG can be used, if necessary or desired. The vector should also possess a complete polyadenylation signal as described by Ausubel et al. (1987) in *Current Protocols in Molecular Biology*, Wiley, so that mRNA transcribed from the vector is properly processed. Finally, the vector may also contain the replication origin and at least one antibiotic resistance marker from a plasmid such as pBR322, to allow replication and selection in *E. coli*.

In order to select a stable cell line that produces the protein of interest, the expression vector can carry the gene for a selectable marker such as a drug resistance marker or a complementary gene for a deficient cell line, such as a dihydrofolate reductase (dhfr) gene for transforming a dhfr⁻ cell line, as described by Ausubel et al., supra. Alternatively, a separate plasmid carrying the selectable marker can be cotransformed along with the expression vector.

Vectors for mammalian cells can be introduced therein by several techniques, including calcium phosphate:DNA coprecipitation, electroporation, or protoplast fusion. Coprecipitation with calcium phosphate as described by Ausubel et al., supra, is the preferred method.

Preferred vectors include, for example, a PSVT7 eukaryotic expression plasmid.

EXAMPLE 1

Cloning of cDNA Encoding Factor OP-1 in the Transfer Vector for Baculovirus

As baculovirus DNA is very extensive (125 Kb), it is necessary to effect recombination between the transfer construct containing the gene of interest and the viral DNA to obtain a recombinant baculovirus. Transfer vector pVL1392 (Invitrogen Corporation, FIG. 2), containing the regulatory regions of polyhedrin up- and down-stream (SEQ. I.D. NO.: 4) from a polylinker containing various restriction sites (SEQ. I.D. NO.: 5 and SEQ. I.D. NO.: 6), was employed. The XbaI and BamHI sites were used for cloning.

The PCR technique was also used for this cloning. Suitable oligonucleotides were synthesized with a solid phase synthesizer by the phosphoramidite method, according to the standard procedure for a 330B DNA Synthesizer (Applied Biosystems, U.S.A.). These oligonucleotides were treated at 55° C. for 12 hours in ammonia and then dried in a vacuum centrifuge. They were resuspended in 2.5M ammonium acetate and then precipitated with 3 volumes of cold ethanol (−20° C.). They were rewashed with 80% cold ethanol and resuspended in water. The concentration of oligonucleotides was determined spectrophotometrically.

The amplification procedure was performed on a Perkin Elmer Cetus DNA Thermal Cycler Amplifier, and the reagents used for amplification were those contained in the GenAmp® kit (Perkin Elmer Cetus).

Briefly, a mixture of 200 µM of each oligonucleotide, 0.5 µM of each of the nucleotides dATP, dCTP, dGTP, and dTTP, 0.1 µg of DNA, and reaction buffer, was prepared in a total volume of 100 µl with 0.5 U of Taq polymerase, and was covered with oil to prevent evaporation. The reaction was conducted setting the instruments at 30 cycles. Each cycle was as follows: 1 min. at 94° C., 2 min. at 50° C., 3 min. at 72° C. The amplified fragments were then purified in LMP or NuSieve agarose using a Geneclean™ kit.

Two oligonucleotides were constructed to start with: OP-PstI, between bases 780 and 750, and OP-NcoI, between bases 250–270, having the following sequences:

OP-PstI: 5' TTGATGCTCTGCCCATCCAGCGT 3' (SEQ. I.D. NO.: 7)

OP-NcoI: 5' CATGCTGGACCTGTACAACGCCAT 3' (SEQ. I.D. NO.: 8)

Figure 3:
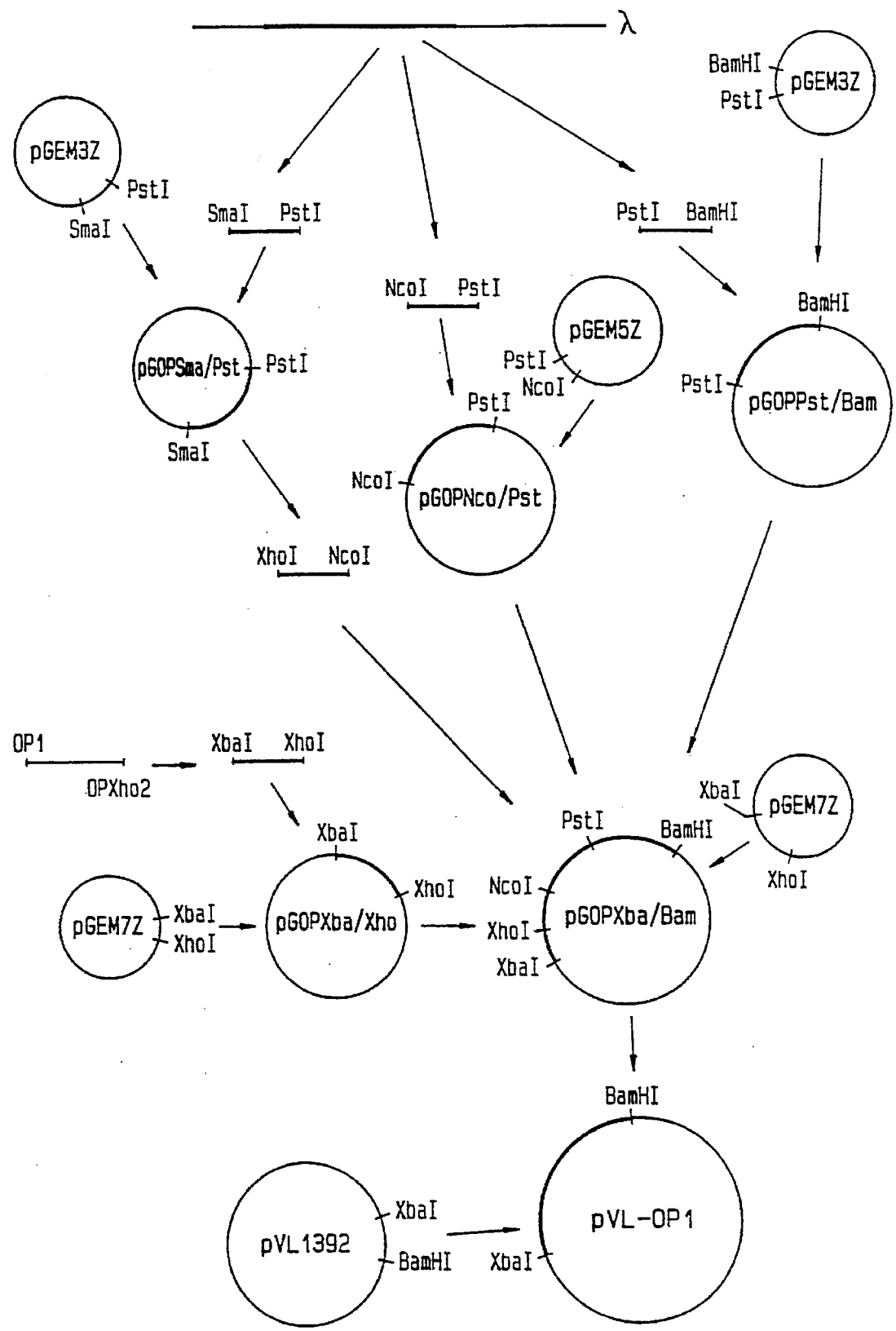
FIG. 3 is a diagram of the scheme employed to clone the cDNA of osteoinductive factor OP-1 in the vector pVL1392 to obtain plasmid pVL-OP1.

A fragment of about 470 bp was amplified from a library of human placental cDNA in λgt11 (Clontech). This fragment was inserted into a pGEM®-5Z vector, the vector obtained being pGOPNco/Pst (FIG. 3). The DNA sequence was checked, and the fragment was then used as a probe to find the gene of interest within the library itself. The library was plated, and the DNA from 500,000 independent plaques was transferred onto nitrocellulose filters. This was followed by hybridization with the labelled probe, and the positive phage plaques containing at least the 470 bp fragment were analyzed further.

For this purpose, the oligonucleotides shown below were constructed:

OP-PstII: 5' GTGGTCAATCCGCGGCACAACCTG 3' (SEQ. I.D. NO.: 9)

OP-Bam: 5' AGGATCCAGCTAGTGGCAGCCACAGG 3' (SEQ. I.D. NO.: 10)

The first oligonucleotide lies next to OP-PstI, amplifying in the opposite direction; the second oligonucleotide supplies a BamHI site for cloning after the stop codon of the gene. The oligonucleotide

OP-1: 5' AATCTAGAATGCACGTGCGCTCCAC 3' (SEQ. I.D. NO.: 11)

creates an XbaI site at the start of the gene.

The amplification reaction between OP-1 and OP-PstI yielded no results, suggesting that the initial portion of the gene was missing, while the terminal portion was present. A fragment between PstI and BamHI was then subcloned from phage λ in a pGEM®-3Z vector, to obtain the vector pGOPPst/Bam (FIG. 3).

Using the oligonucleotide OP-PstI and a commercial oligonucleotide positioned on phage λ (Lambda gt11 primer (forward), #1218, 5' GGTGGCGACGACTCCTGGAGC-CCG 3' (SEQ. I.D. NO.: 12), New England Bio Labs), a new portion of the gene was amplified. This amplified fragment was phosphorylated at the 5' end, and then cloned in a pGEM®-3Z vector as a SmaI/PstI fragment, producing the vector pGOPSma/Pst (FIG. 3). The sequence of the construct was then analyzed, revealing the absence of the first 121 nucleotides of the gene.

A long oligonucleotide of 108 bases was then prepared (underlined in the gene sequence shown in FIG. 1), and two primers, one towards the 5' end and the other towards the 3' end around position 11 which represents an XhoI site were prepared:

OP-XhoI: 5' CACTCGAGCTTCATCCACCGGCGCC 3' (SEQ. I.D. NO.: 13)

OP-XhoII: 5' AGCTCGAGTGCACCTCGTTGTCCAGGCTGAA 3' (SEQ. I.D. NO.: 14).

Another oligonucleotide was then constructed:

OP-NcoII: 5' TTGTAGGGGTAGGAGAAGCCCTG 3' (SEQ. I.D. NO.: 15).

positioned near OP-NcoI, but amplifying in the opposite direction.

Using the primer OP-XhoII and the primer OP-1 on the fragment of 108 nucleotides, an XbaI/XhoI fragment was amplified, which was in turn subcloned in a pGEM®-7Z vector (FIG. 3). The vector thus obtained was pGOPXba/Xho (FIG. 3).

On the SmaI/PstI fragment, previously cloned in the pGEM®-3Z vector, amplifying with the primers OP-XhoI and OP-NcoII, produced another XhoI/NcoI fragment to be used later for the final cloning.

Once the fragments had been checked, the final cloning in a pGEM®-7Z vector was carried out. From this, the entire fragment was transferred into the pVL1392 vector (Invitrogen). The final vector obtained was called pVL-OP1 (FIG. 3).

Placement of the various primers along the gene may be summarized as follows:

5' OP-1    OP-Xho$_I$    OP-Nco$_I$    OP-Pst$_{II}$
    OP-Xho$_{II}$    OP-Nco$_{II}$    OP-Pst$_I$    OP-Bam 3'

EXAMPLE 2

Insect Cell Cultures

The methods of culturing these cells are well known to those working in this technology. Procedures for their cultivation are disclosed in Summers, M. D. et al. 1987, EP Publication No. 127 839, and Smith G. E., U.S. Pat. No. 4,745,051.

For the purpose of present invention, *Spodoptera frugiperda* Sf9 cells, which can be grown in monolayers or in suspension, were employed. *Spodoptera frugiperda* Sf21 cells can also be employed.

Monolayers were incubated at 27° C., and divided two or three times a week, when they reach confluence. Conditions required by cultures in suspension depend on the culture medium and the volume of the culture. About two million cells per ml are grown in fermenters. The culture medium is enriched with a Pluronic F68 protective agent to prevent the cells from being damaged when shaken.

The culture media used were Bink's TNM-FH (J.R.H. Biosciences) +10% fetal calf serum, or EXCELL401 (J.R.H. Biosciences).

EXAMPLE 3

Preparation and Isolation of the Recombinant Virus

Details of the methods employed to isolate the recombinant virus are described in European patent No. 0 127 839. Generally, 2 µg of DNA of the transfer vector carrying the DNA coding for OP-1 and 1 µg of AcMNPV viral DNA are cotransfected in a monolayer of *Spodoptera frugiperda* cells. The cells show viral occlusions after 3–4 days, and 10–50% of the cells are infected. The virus passes into the culture medium with a titer of about $10^7$–$10^8$, and of this, 0.1–0.5% are recombinant viruses. Once the supernatant has been obtained, purification of the recombinant virus can begin. The procedure consists of associating a limiting dilution with dot-blot hybridization.

The cells are seeded in a 96-well dish at a concentration of $2\times10^4$ cells per well. They are then infected with serial dilutions of $10^{-1}$ to $10^{-8}$ of supernatant. The dishes are incubated at 27° C., and infection is monitored. After 8–10 days, the supernatant is transferred into another dish and the cells are lysed. The DNA from each well is transferred onto a nylon membrane (Hybond-N) using a dot-blot apparatus, and it is then fixed by U.V. for 3 minutes. Once fixed, the 470 bp fragment of OP-1, NcoI/PstI, is hybridized according to conventional techniques using $^{32}$P-labelled probe.

The viral supernatant corresponding to the positive clone is subjected to this procedure once more. Usually, three cycles of treatment produce a pure recombinant virus that no longer produces polyhedrin molecules, but only recombinant protein molecules.

Once recombinant virus Containing DNA encoding osteoinductive factor OP-1 has been obtained, it is amplified and production is begun.

EXAMPLE 4

Protein Analysis

The protein obtained from infected cells was analyzed by electrophoresis in polyacrylamide gels and by Western blotting using polyclonal antibodies that recognize amino acid sequences within the OP-1 sequence.

Two antibodies were prepared against two synthetic peptides prepared with a 9050 Pepsynthesizer™ (Milligen), the first being positioned between amino acids 300–320, and the second between amino acids 290–310. A third was prepared using as antigen a protein fragment corresponding to the mature portion of the protein expressed in *E. coli*. This polypeptide can be used to check that factor OP-1 has in fact been processed in *Spodoptera frugiperda* cells.

FIG. 4 shows the results of polyacrylamide gel electrophoresis under reducing conditions and Western blotting with the antipeptide antibody 300–320 of an initial preparation of the OP-1 factor in the insect cells. From this figure, it is possible to see the location of polypeptide OP-1 on the gel, as shown by the arrows, with different degrees of glycosylation.

EXAMPLE 5

Pharmaceutical Compositions

Osteogenic protein, OP-1, prepared by the method of the present invention can be employed to produce pharmaceutical compositions comprising conventional pharmaceutically acceptable carriers. In such pharmaceutical compositions, OP-1 can be present in an amount from 0.1 to 99% by weight, preferably 5 to 80% by weight, and more preferably from 10 to 70% by weight of the total composition.

Such pharmaceutical compositions are useful in the treatment of bone defects, for the formation and/or repair or regeneration of bones and cartilage, for the treatment of bone diseases and orthopedic diseases, for the treatment of osteoporosis and osteoarthritis, and for bone recovery following trauma by fracture.

The utility of OP-1 in such pharmaceutical compositions can be attributed to the fact that OP-1 prepared by the method of the present invention possesses the biological activity of naturally-occurring OP-1.

The present inventors have been the first to successfully produce biologically active OP-1 by recombinant techniques using baculovirus-infected insect cells. OP-1 is a complex protein, and the production thereof in biologically active form has been fraught with difficulties.

Among these, it should be noted that OP-1 is a complex protein that is translated in precursor form. Further processing of the precursor requires attack in the $NH_2$-terminal region. The pre-pro region appears to be essential for obtaining the biologically active protein. Furthermore, the pre-pro region is glycosylated, and this glycosylation is important in obtaining biologically active OP-1. Finally, via the instant method, OP-1 is secreted into the culture medium.

Thus, this is the first demonstration of the successful production of biologically active OP-1 using the baculovirus expression system.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for preparing a recombinant baculovirus capable of expressing osteogenic protein, OP-1, in insect cells, comprising:
    (a) inserting a DNA sequence encoding said OP-1 into a baculovirus transfer vector to produce a transfer vector containing said DNA sequence;
    (b) cotransfecting an insect cell with said transfer vector containing said DNA sequence of step (a) and wild-type *Autographa californica* multiple nuclear polyhedrosis virus, AcMNPV, viral DNA; and
    (c) recovering recombinant baculovirus containing said DNA sequence encoding OP-1.

2. The method of claim 1, wherein said DNA sequence encoding OP-1 is a human cDNA sequence.

3. The method of claim 2, wherein said cDNA sequence encoding OP-1 is produced by a method comprising:
    (a) amplifying, by the polymerase chain reaction technique, successive or successive overlapping fragments of DNA encoding OP-1 by employing appropriately spaced oligonucleotide primers encoding restriction endonuclease sites; and (b) assembling said fragments by recombinant DNA techniques to produce a DNA sequence encoding osteogenic protein, OP-1.

4. The method of claim 3, wherein said oligonucleotide primers of step (a) are selected from the group consisting of SEQ. I.D. NO.: 7, SEQ. I.D. NO.: 8, SEQ. I.D. NO.: 9, SEQ. I.D. NO.: 10, SEQ. I.D. NO.: 11, SEQ. I.D. NO.: 13, SEQ. I.D. NO.: 14, and SEQ. I.D. NO.: 15.

5. The method of claim 3, wherein said fragments are selected from the group of fragments consisting of SmaI-PstI, NcoI-PstI, PstI-BamHI, XhoI-NcoI, and XbaI-XhoI.

6. The method of claim 1, wherein said baculovirus transfer vector is pVL1392.

7. The method of claim 1, wherein said transfer vector containing said DNA sequence is pVL-OP1.

8. The method of claim 1, wherein said insect cell is a member selected from the group consisting of a *Spodoptera frugiperda* Sf9 cell and a *Spodoptera frugiperda* Sf21 cell.

9. A recombinant baculovirus, wherein said baculovirus comprises a DNA sequence encoding human osteogenic protein, OP-1, functionally linked to regulatory elements necessary for the expression of OP-1 in insect cells infected with said recombinant baculovirus.

10. The recombinant baculovirus of claim 9, wherein said DNA sequence encoding human osteogenic protein, OP-1, is functionally linked to the promoter for the polyhedrin gene of baculovirus.

11. A recombinant baculovirus produced by the method of claim 1.

12. An insect cell harboring said recombinant baculovirus prepared by the method of claim 3.

13. The insect cell of claim 12, wherein said insect cell is selected from the group consisting of a cell of *Spodoptera frugiperda* Sf9 and a cell of *Spodoptera frugiperda* Sf21.

14. A method for producing osteogenic protein, OP-1, comprising:

(a) inserting a DNA sequence encoding said OP-1 into a transfer vector capable of introducing said sequence into the genome of baculovirus, thereby producing recombinant baculovirus;

(b) introducing said recombinant baculovirus into an insect cell;

(c) culturing said insect cell harboring said recombinant baculovirus; and (d) recovering said OP-1 expressed during said culturing of step (c).

15. Transfer vector pVL-OP1.

* * * * *